United States Patent
Riley

(10) Patent No.: US 7,692,054 B2
(45) Date of Patent: Apr. 6, 2010

(54) PROCESS AND APPARATUS FOR ALKYLATION OF AROMATIC COMPOUND WITH ALIPHATIC MONO-OLEFIN COMPOUND OF 8 TO 18 CARBON ATOMS

(75) Inventor: Mark G. Riley, Hinsdale, IL (US)

(73) Assignee: UOP LLC, Des Plaines, IL (US)

( * ) Notice: Subject to any disclaimer, the term of this patent is extended or adjusted under 35 U.S.C. 154(b) by 133 days.

(21) Appl. No.: 11/872,786

(22) Filed: Oct. 16, 2007

(65) Prior Publication Data

US 2008/0161617 A1    Jul. 3, 2008

Related U.S. Application Data

(60) Provisional application No. 60/863,441, filed on Oct. 30, 2006.

(51) Int. Cl.
  *C07C 2/56* (2006.01)
(52) U.S. Cl. ........................... 585/449; 585/455
(58) Field of Classification Search ................. 585/449, 585/455
  See application file for complete search history.

(56) References Cited

U.S. PATENT DOCUMENTS

| | | | |
|---|---|---|---|
| 5,196,574 A | 3/1993 | Kocal | 562/94 |
| 5,777,187 A | 7/1998 | Knifton et al. | 585/449 |
| 6,187,981 B1 | 2/2001 | Marinangeli et al. | 585/323 |
| 6,232,515 B1 * | 5/2001 | Schulz et al. | 585/323 |
| 6,315,964 B1 | 11/2001 | Knifton et al. | 422/190 |
| 6,617,481 B1 | 9/2003 | Kulprathipanja et al. | 585/323 |
| 6,670,516 B1 | 12/2003 | Marinangeli et al. | 585/323 |
| 2003/0147805 A1 | 8/2003 | Koegler et al. | 423/700 |
| 2006/0224028 A1 | 10/2006 | Ayoub et al. | 585/319 |
| 2006/0224031 A1 | 10/2006 | Jan et al. | 585/467 |
| 2008/0161619 A1 | 7/2008 | Riley et al. | |
| 2008/0161621 A1 | 7/2008 | Riley et al. | |

OTHER PUBLICATIONS

Pujado, P.R.; "Linear Alkylbenzene (LAB) Manufacture" Handbook of Petroleum Refining Processes, edited by Robert A. Meyers, 2nd Edition, McGraw-Hill, New York, NY, USA (1996), pp. 1.53-1.66.

* cited by examiner

*Primary Examiner*—Thuan Dinh Dang
(74) *Attorney, Agent, or Firm*—Arthur E Gooding

(57) ABSTRACT

Continuous processes for monoalkylating aromatic compound with an aliphatic feedstock comprising aliphatic olefin of 8 to 18 carbon atoms per molecule are effected using at least 3 reaction zones in series, each containing solid alkylation catalyst with effluent cooling between reaction zones, each of which reaction zones is supplied a portion of the fresh aliphatic feedstock, such that the Reaction Zone Delta T in each reaction zone is less than about 15° C. The overall aromatic compound to olefin molar ratio is less than about 20:1. The alkylation product has desirable linearity and low amounts of dimers, dealkylated compounds and diaryl compounds even though a low aromatic compound to olefin molar ratio is used.

7 Claims, 2 Drawing Sheets

PROCESS AND APPARATUS FOR ALKYLATION OF AROMATIC COMPOUND WITH ALIPHATIC MONO-OLEFIN COMPOUND OF 8 TO 18 CARBON ATOMS

CROSS-REFERENCE TO RELATED APPLICATIONS

This application claims priority to Provisional U.S. Application No. 60/863,441, filed on Oct. 30, 2006, all of which is incorporated by reference.

BACKGROUND OF THE INVENTION

This invention relates to economically attractive processes and apparatus for the alkylation of aromatic compound with mono-olefin aliphatic compound of 8 to 18 carbon atoms at low aromatic compound to mono-olefin molar ratios to provide a mono-alkylated reaction product having low co-production of heavies (dimers, polyalkylated compounds and diarylalkanes). The processes and apparatus of this invention are particularly attractive for the alkylation of benzene with linear and slightly branched olefins to provide linear alkylbenzenes and modified linear alkylbenzenes having reduced skeletal isomerization.

Alkylation of benzene produces alkylbenzenes that may find various commercial uses, e.g., alkylbenzenes can be sulfonated to produce detergents. In the alkylation process, benzene is reacted with an olefin the desired length to produce the sought alkylbenzene. The alkylation conditions comprise the presence of homogeneous or heterogeneous alkylation catalyst such as aluminum chloride, hydrogen fluoride, or zeolitic catalysts and elevated temperature.

The catalysts are not selective and other reactions of olefins can occur to produce heavies, i.e., dimers, dialkylaryl compounds and diaryl compounds. Also, skeletal isomerization of the olefin can occur, resulting in a loss of selectivity to the sought alkylbenzene. The formation of dialkylaryl compounds is particularly problematic as the reaction approaches complete conversion of the olefin and the concentration of the alkylbenzene has thus increased thereby increasing the likelihood that an olefin molecule will react with an alkylbenzene molecule rather than benzene. Accordingly, typical processes use a large excess of benzene relative to the olefin to reduce the molar ratio of the sought alkylbenzene to the olefin in the reactor. For homogeneous hydrogen fluoride catalyzed processes, the benzene to olefin ratio is generally in the range of 6:1 to 8:1. Solid catalysts are prone to generate more heavies. Hence, for these solid catalysts the mole ratio of benzene to olefin is typically greater than 15:1. For making alkylbenzenes with reduced skeletal isomerization, the benzene to olefin ratio is often in excess of 20:1 and sometimes as much as 30:1.

As the ratio of benzene to olefin increases, additional process costs are also incurred in the recovery and recycling of the unreacted benzene in the alkylation product. The refining system for alkylbenzene production is summarized in Peter R. Pujado, *Linear Alkylbenzene (LAB) Manufacture*, Handbook of Petroleum Refining Processes, edited by Robert A. Meyers, Second Edition, McGraw-Hill, New York, N.Y., USA, (1996), pp 1.53 to 1.66, especially pages 1.56 to 1.60. Especially for large-scale, commercial alkylation processes such as are used for the production of linear alkylbenzenes, capital and operating costs can be very important, and the addition of additional distillation steps can thus be undesirable.

A number of proposals have been made to achieve some of the benefits of high benzene to olefin feed ratios without having to incur the costs associated with using such excesses of benzene. For instance, the use of more than one reaction zone with the olefin-containing feed being introduced into each of the reactors is often done. This process has the advantage of being inexpensive from a capital and operating cost standpoint. Others have proposed processes to further improve selectivity without further increasing the molar ratio of benzene to olefins. U.S. Pat. No. 5,777,187 discloses the use of reactive distillation where benzene and the olefin are passed countercurrently though a column containing catalyst. Two problems exist with this approach. First, the capital and operating expense are increased. Second, as the catalyst needs to be regenerated or replaced, the entire reactive distillation column needs to be shut down.

Another proposal is to have a multistage reactor with product separation by distillation between the stages with the benzene and unreacted olefin passed to the subsequent reactor. However, such a process suffers from increased capital and operating costs associated with inter-stage fractionation. For example, benzene columns for removal of benzene from alkylbenzene reaction product often have at least 20 theoretical distillation trays.

One of the benefits that arises from the advent of commercially viable alkylation processes using solid alkylation catalysts is the avoidance of the use of hydrogen fluoride. As stated above, the hydrogen fluoride process, however, does benefit from being able to operate with a low benzene to olefin molar ratio, often below 8:1, without undue production of heavies or without undue skeletal isomerization.

Accordingly processes and apparatus are sought for solid catalyst alkylation of aromatic compound with mono-olefin of 8 to 18, preferably 8 to 16, carbon atoms per molecule which can use lower aromatic compound to olefin molar ratios without undue production of heavies, especially if such processes do not result in undue skeletal isomerization. Also desired are solid catalyst alkylation processes and apparatus that can retrofit a hydrogen fluoride catalyst alkylation unit without the need to replace any of the reaction product refining system, especially the benzene distillation column. Consequently, the retrofit must be capable of providing an alkylation product of sought yields using an aromatic compound to olefin molar ratio of about 10:1 or less.

SUMMARY OF THE INVENTION

In accordance with this invention, energy efficient, solid catalyst processes and apparatus for mono-alkylating aromatic compound with aliphatic olefin of 8 to 18, preferably 8 to 16, carbon atoms per molecule are provided that are capable of yielding the sought alkylaromatic with little coproduction of heavies and without undue skeletal isomerization, yet use an aromatic compound to olefin molar ratio of less than about 20:1, and even less than about 10:1.

The processes and apparatus of the invention use a reactor assembly having at least 3 substantially adiabatic alkylation reaction zones in series wherein a portion of the olefin-containing feed is fed to each zone in an amount such that the increase in temperature between that of the feed and that of the reaction zone or of the reaction zone effluent is less than about 15° C., preferably less than about 12° C., and most preferably less than about 10° C., and wherein the effluent from each zone is cooled prior to passing to a subsequent zone for reaction with a further portion of the olefin-containing feed.

In the broad aspects of the continuous processes of this invention for monoalkylating aromatic compound of 6 to 8 carbon atoms per molecule with an aliphatic feedstock comprising paraffin and mono-olefin of 8 to 18, preferably 8 to 16, carbon atoms per molecule in an alkylation reactor assembly having at least 3, preferably at least 4, say, 4 to 10, reaction zones in series, each reaction zone comprising solid alkylation catalyst and being maintained under liquid phase alkylation conditions sufficient to consume at least about 90 mass percent of the olefin to produce a zone effluent comprising arylalkane, wherein the molar ratio of total aromatic compound to total mono-olefin passed to the alkylation reactor assembly is less than about 20:1, preferably less than about 15:1, and most preferably between about 6:1 to 12:1, comprise:

a. co-currently passing said aromatic compound and a portion of the aliphatic feedstock at a first blend temperature to the first reaction zone to produce a first zone effluent, the mass ratio of said aromatic compound to said aliphatic feedstock being sufficient that the temperature of the first zone effluent is less than 15° C., preferably less than about 12° C., and most preferably less than about 10° C., above the blend temperature;

b. cooling the first zone effluent;

c. co-currently passing at least a portion of said cooled first zone effluent and another portion of the aliphatic feedstock at a second blend temperature to a second reaction zone to produce a second zone effluent comprising arylalkane, the mass ratio of said aromatic compound to said aliphatic feedstock being sufficient that the temperature of the second zone effluent is less than 15° C., preferably less than about 12° C., and most preferably less than about 10° C., above the blend temperature (Reaction Zone Delta T);

d. repeating steps (b) and (c) using the preceding zone effluent after cooling and another portion of the aliphatic feedstock at a blend temperature for that subsequent reaction zone a sufficient number of times to use the aliphatic feedstock.

The cooling of each zone effluent may be by direct or indirect heat exchange, and is preferably at least partially effected by direct heat exchange with the portion of the aliphatic feedstock being passed to the zone, the aliphatic feedstock being provided at a cooler temperature than the preceding zone effluent. The cooling is often sufficient to reduce the temperature increased experienced in the previous reaction zone by at least 60 percent, and preferably the temperature reduction is at least to that of the blend temperature of the previous reaction zone.

In one embodiment of the processes of this invention, substantially the same amount of fresh aliphatic feedstock is fed to each reaction zone. In another embodiment, the amount of fresh aliphatic feedstock fed to the first reaction zone is less than that fed to at least one subsequent zone. In this latter embodiment, the Reaction Zone Delta T experienced in the first reaction zone will be reduced. Where the aliphatic feedstock contains less than about 15 mass percent olefin with the balance being substantially inert paraffins, as is often the case with aliphatic feedstocks available for commercially practiced alkylation processes, the paraffins act as a heat sink. The first reaction zone will only be fed that amount of paraffin contained in the portion of the aliphatic feedstock fed to it, whereas subsequent reaction zones will have not only the paraffin contained in the aliphatic feedstock, but also that amount of paraffin contained in the effluent from the previous reaction zone. Hence the earlier in the series reaction zones contain less heat sink than do the subsequent reaction zones.

In a preferred aspect, the amounts of fresh aliphatic feedstock fed to each reaction zone are such that the range of Reaction Zone Delta T among the reaction zones is less than about 5° C., preferably less than about 3° C.

In preferred processes, a trim reaction zone containing solid alkylation catalyst is employed at the end of the series of reaction zones. The trim reaction zone does not receive any portion of the aliphatic feedstock but rather is maintained under liquid phase alkylation conditions sufficient to consume substantially all olefin contained in the zone effluent from the last of the zones.

In the broad aspects of this invention, the alkylation apparatus comprises:

a. a distributor adapted to distribute portions of an aliphatic feedstock comprising paraffin and mono-olefin of 8 to 18, preferably 8 to 16, carbon atoms per molecule;

b. a reactor assembly comprising at least three alkylation reaction zones in series each containing solid alkylation catalyst and each having an inlet region and in fluid flow opposition through the catalyst, an outlet region adapted to contain reaction zone effluent, i. the first of which is adapted to receive at the inlet region aromatic compound and receive at the inlet region from the distributor a portion of the aliphatic feedstock;

ii. the remaining reaction zones of which are adapted to receive at the inlet region reaction zone effluent from the preceding reaction zone in the series and adapted to receive at the inlet region a portion of the aliphatic feedstock from the distributor, and c. a heat exchanger between each of the reaction zones adapted to cool the reaction zone effluent of the preceding reaction zone by at least about 5° C., and preferably at least about 10° C.

Preferably the apparatus of the invention further includes a trim alkylation reaction zone containing solid alkylation catalyst and adapted to receive reaction zone effluent from the last of the remaining reaction zones. Each heat exchanger may be of a direct, indirect or combination of direct and indirect heat exchanger design. Preferably the heat exchange is at least partially by direct heat exchange using the portion of the aliphatic feedstock to the subsequent reaction zone.

DETAILED DISCUSSION OF THE INVENTION

The Feed and Products

Figure 1:
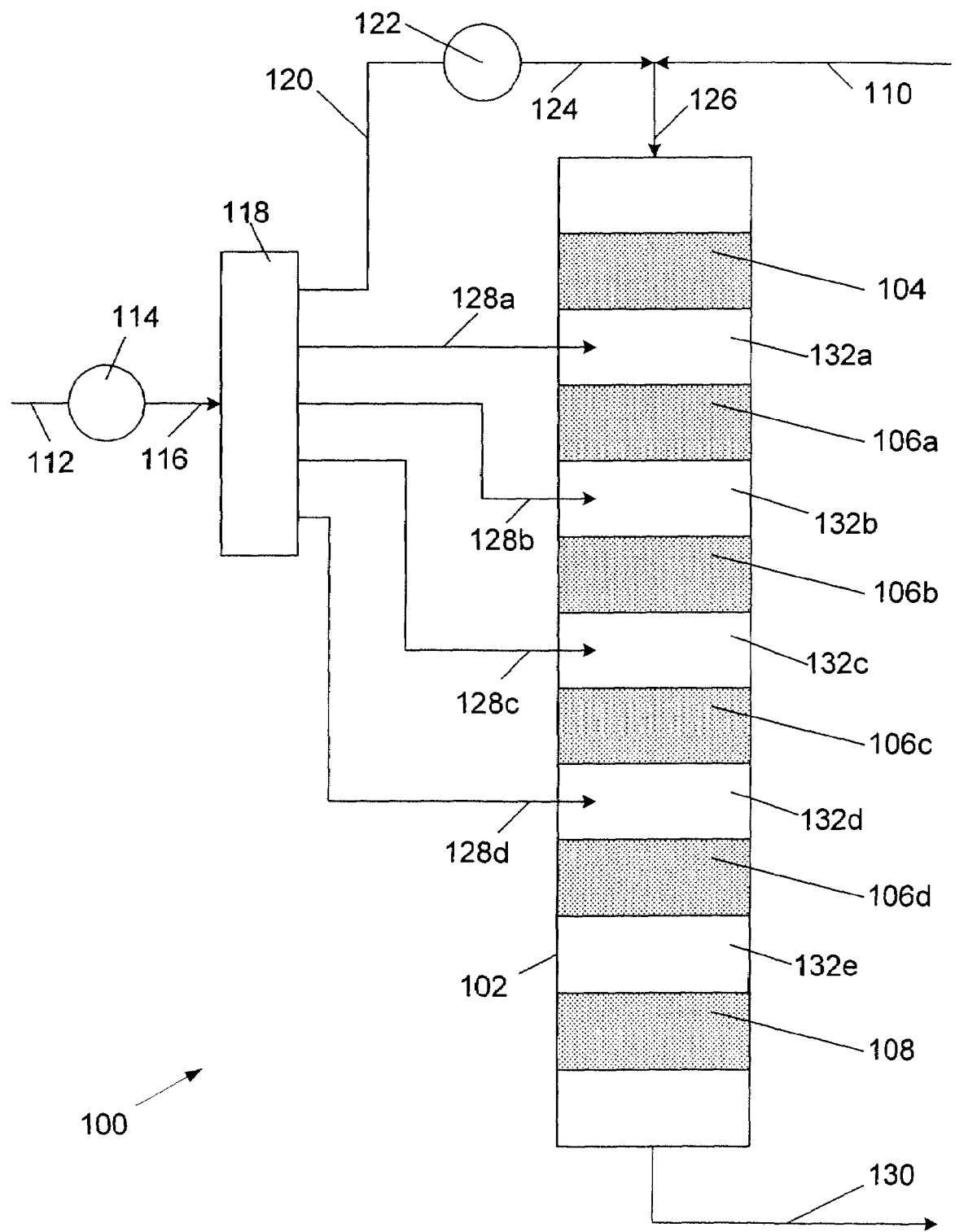
FIG. 1 is a schematic representation of an apparatus adapted to practice a process in accordance with this invention.

The aliphatic feedstock used in the processes of this invention contains aliphatic mono-olefin of 8 to 18, preferably 8 to 16, more preferably 8 to 14, carbon atoms per molecule. The aliphatic olefin is usually a mixture of olefins having different molecular weights. The olefin may be an alpha-olefin or comprise a mixture of olefin isomers. In most instances, the positioning of the olefinic bond in the molecule is not critical as most solid alkylation catalysts have been found to promote migration of the olefinic bond.

The branching of the hydrocarbon backbone is often a concern as the structural configuration of the alkyl group on the alkylaromatic product can affect performance. For instance, where alkylbenzenes are sulfonated to produce surfactants, undue branching can adversely affect the biodegradability of the surfactant. On the other hand, some branching may be desired such as the lightly branched modified alkylbenzenes such as described in U.S. Pat. No. 6,187,981B1. The olefin may be unbranched or lightly branched, which as used herein, refers to an olefin having three or four primary carbon atoms and for which none of the remaining carbon atoms are quaternary carbon atoms. A primary carbon atom is a carbon atom which, although perhaps bonded also to other atoms besides carbon, is bonded to only one carbon atom. A quaternary carbon atom is a carbon atom that is bonded to four other carbon atoms.

For commercial processes, other components may be present in the aliphatic feedstock with the olefin-containing aliphatic compound. These other components may comprise paraffins of 8 to 18, or 8 to 16, or 8 to 14, carbon atoms per molecule. For instance, the olefin may be obtained by the dehydrogenation of a paraffinic feedstock and unreacted paraffin, which is difficult to separate from the olefin, is passed to the alkylation reactor. See, for instance, U.S. Pat. No. 6,670,516B1, herein incorporated by reference. Generally, where olefin is obtained by the dehydrogenation of a paraffinic feedstock, the molar ratio of olefin to paraffin is between about 1:12 to about 1:7 or the molar ratio of mono-olefin to paraffin is between about 1:12 to about 1:7; however, such amounts of paraffin are not critical to the processes of this invention. Indeed, aliphatic feedstocks having an essential absence of paraffins are suitable.

The source of the paraffinic feedstock for dehydrogenation is not critical although certain sources of paraffinic feedstocks will likely result in the impurities being present. Conventionally, kerosene fractions produced in petroleum refineries either by crude oil fractionation or by conversion processes therefore form suitable feed mixture precursors. Fractions recovered from crude oil by fractionation will typically require hydrotreating for removal of sulfur and/or nitrogen prior to being fed to the subject process. The boiling point range of the kerosene fraction can be adjusted by prefractionation to adjust the carbon number range of the paraffins. In an extreme case the boiling point range can be limited such that only paraffins of a single carbon number predominate. Kerosene fractions contain a very large number of different hydrocarbons and the feed mixture to the subject process can therefore contain 200 or more different compounds.

The paraffinic feedstock may alternatively be at least in part derived from oligomerization or alkylation reactions. Such feed mixture preparation methods are inherently imprecise and produce a mixture of compounds. The feed mixtures to the process may contain quantities of paraffins having multiple branches and paraffins having multiple carbon atoms in the branches, cycloparaffins, branched cycloparaffins, or other compounds having boiling points relatively close to the desired compound isomer.

Another source of paraffins is in condensate from gas wells. Usually insufficient quantities of such condensate are available to be the exclusive source of paraffinic feedstock. However, its use to supplement other paraffinic feedstocks can be desirable. Typically these condensates contain sulfur compounds, which have restricted their use in the past. As this invention enables the use of sulfur-containing feeds, these condensates can be used to supply paraffins for alkylation.

Paraffins may also be produced from synthesis gas (Syngas), hydrogen and carbon monoxide. This process is generally referred to as the Fischer-Tropsch process. Syngas may be made from various raw materials including natural gas and coal, thus making it an attractive source of paraffinic feedstock where petroleum distillates are not available.

The aliphatic olefin to the alkylation reactor should be sufficiently free of impurities, such as water, nitrogen compounds and sulfur compounds, that can unduly adversely affect the life of the alkylation catalyst.

The aromatic compound used in the process of this invention comprises 6 to 8 carbon atoms per molecule such as toluene, xylene, ethylbenzene, and preferably benzene.

Alkylation:

Aromatic compound and the olefin are reacted under alkylation conditions in the presence of a solid alkylation catalyst. These alkylation conditions generally include a temperature in the range between about 80° C. and about 200° C., most usually at a temperature not exceeding about 175° C., e.g., 100° C. to 160° C. Typically, as the catalyst ages, the temperature of the alkylation is increased to maintain desired activity. The alkylation is an exothermic reaction and thus in a substantially adiabatic reactor, the effluent is at a higher temperature than that of the feed (Reaction Zone Delta T). A substantially adiabatic reactor is one where the increase in temperature of the effluent over that of the feed accounts for at least about 75 percent of heat generated by the reactions in the reaction zone.

Heretofore the temperature within a reaction zone has been maintained within a suitable range by providing a large excess of aromatic compound to the reaction zone to absorb heat. Where the aliphatic feedstock contains paraffins, the paraffins also serve to absorb heat from the exothermic reactions. High exothermic temperatures during the alkylation can result in untoward effects in terms of not only catalyst deactivation but also in product quality degradation, especially skeletal isomerization, and, in particular, skeletal isomerization of the olefin.

In accordance with the processes of this invention, lower overall aromatic compound to aliphatic feedstock ratios (benzene to olefin ratios in the case of alkylbenzene) can be used while providing an alkylated product of sought quality resulting in savings in recovery and recycling of the aromatic compound as well as the ability to retrofit HF alkylation process facilities to use solid alkylation catalyst. In accordance with the processes of this invention, the molar ratio of aromatic compound to olefin is less than about 20:1, preferably less than about 15:1, and most preferably between about 6:1 and 12:1. Preferably, less than 15 mole percent, and more preferably less than 10 mole percent, of the olefin, the aliphatic alkyl chain, and any reaction intermediate undergoes skeletal isomerization.

The ratio of aromatic compound (or preceding reaction zone effluent with respect to the subsequent reaction zones in the series) to aliphatic feedstock fed to each reaction zone in accordance with the processes of this invention is selected such that the Reaction Zone Delta T is less than about 15° C., preferably less than about 12° C., and most preferably less than about 10° C., most often between about 2° C. to 10° C. Preferably the amount of aliphatic feedstock to each reaction zone is such that no reaction zone has a Reaction Zone Delta T greater than about 5° C. than any other reaction zone. Preferably, the difference in the Reaction Zone Delta T among the reaction zones is less than about 5° C.

Since the alkylation is typically conducted in the presence of a liquid phase, and preferably in either an all-liquid phase or at supercritical conditions, pressures must be sufficient to maintain reactants in the liquid phase. The requisite pressure necessarily depends upon the olefin and temperature, but normally is in the range of about 1300 to 7000 kPa(g), and most usually between about 2000 and 3500 kPa(g).

Alkylation of benzene by the olefins is conducted in a continuous manner using three or more catalyst beds in flow series. For purposes herein, a catalyst bed is termed a reaction zone whether in the same or a separate vessel from another bed. Each reaction zone has an inlet region and an outlet region. The reactants may be in admixture prior to entering the inlet region of the reaction zone, or they may be individually introduced and mixed in the reaction zone.

The catalyst may be used as a packed bed, a moving bed or a slurry bed. The feed to the reaction zone may be passed either upflow or downflow, or even horizontally as in a radial bed reactor; however, the flows of the aromatic compound and olefin are co-current. In one desirable variant, olefin may be fed into several discrete points within the reaction zone. The feed mixture, that is, aromatic compound and aliphatic feedstock to a reaction zone, is often provided at an overall liquid hourly space velocity (overall LHSV) between about 0.3 and about 6 or 10 $hr^{-1}$, and most frequently between about 0.4 and 6 $hr^{-1}$ depending upon, e.g., alkylation temperature and the activity of the catalyst. The overall LHSV is determined from the LHSV's of each of the beds. The reciprocal of the overall LHSV is the sum of the reciprocals of the LHSV of each of the beds in series.

It is usually desired that sufficient residence time in the reaction zone be used such that at least about 90, often at least about 95, preferably at least about 98, and often at least about 99.5, mass percent of the olefin fed to a reaction zone is reacted in that reaction zone.

Any suitable solid alkylation catalyst may be used in the present invention, provided that the requirements for conversion, selectivity, and activity are met. Typically the catalysts are acidic. Preferred alkylation catalysts comprise zeolites having a zeolite framework type selected from the groups consisting of beta, MOR, MWW, FAU and NES. Suitable zeolites include mordenite, ZSM-4, ZSM-12, ZSM-20, offretite, gmelinite, beta, NU-87, UZM-8, MCM-22, MCM-36, MCM-49, zeolite Y, zeolite X, and gottardite. The MOR, MWW, FAU, NES, and other zeolite framework types are described in Ch. Baerlocher, W. M. Meier and D. H. Olson, "Atlas of Zeolite Framework Types," $5^{th}$ Ed., Elsevier: Amsterdam, 2001, herein incorporated by reference. The FAU and UZM-8 molecular sieves may have any convenient particle size. Often the particle sizes of the molecular sieves range upwards of 5 microns or more in major dimension, say, about 50 to 5000, nanometers in major dimension. Particle sizes in the lower portion of the range are sometimes preferred as the coproduction of heavies may be reduced. Major particle dimensions of less than about 500, e.g., from about 50 to 300, nanometers are often desirable. See, for instance, Koegler, et al., US Application Publication No. 2003/0147805A1. Co-pending patent application Ser. No. 11/872,783, filed on even date herewith, discloses processes for making alkylbenzenes at low aromatic compound to olefin mole ratios without undue heavies co-production by using small size FAU crystallite catalyst. Another class of acidic, solid catalysts are acidified refractory oxides such as chlorided, fluorided, or sulfated alumina, gallia, boria, molybdia, ytterbia, titania, chromia, silica, zirconia, and the like and combinations thereof. Clays and amorphous catalysts may also find utility. Further discussion of alkylation catalysts can be found in U.S. Pat. Nos. 5,196,574; 6,315,964B1 and 6,617,481B1.

The same or different catalyst may be used in each reaction zone of the alkylation reactor assembly of this invention.

The reactor assembly of this invention contains at least 3, preferably at least 4, and most frequently between about 4 and 10, reaction zones in series to which a portion of the aliphatic feedstock is fed. Often a trim alkylation reaction zone follows the series to react residual olefin in the effluent from the last reaction zone in series. The reaction zones may be in a common vessel or in separate vessels. The reaction zones may be the same or different sizes. Additional reaction zones may be used in parallel.

The number of reaction zones in series will be related to the sought overall aromatic compound to aliphatic feed ratio to the alkylation reactor assembly and the sought Reaction Zone Delta T. For example, for a given ratio, more reaction zones will be required to achieve a given Reaction Zone Delta T than for a higher Reaction Zone Delta T.

A heat exchanger is provided between each of the reaction zones in the series. If desired, a heat exchanger can be provided immediately upstream of any trim reaction zone, but the use of such a heat exchanger is not required in the broad aspects of the invention. As used herein, a heat exchanger is a unit operation which provides controlled cooling of the effluent from the preceding reaction zone by direct, indirect or a combination thereof heat exchange and does not refer to ambient heat loss. The amount of cooling to be effected between each reaction zone can be varied widely. Generally, the cooling is at least sufficient to remove at least about 75 percent of the heat generated in the preceding reaction zone. The cooled effluent is often at a temperature at least 5° C., and sometimes between 5° C. and 20° C., lower than the temperature of the effluent fed to the heat exchanger. Often the cooling is sufficient to provide the effluent at substantially the same temperature as the feed to the preceding reaction zone. In one embodiment, the cooling of the effluent is sufficient to reduce the temperature of the effluent by a least an amount of 60 percent of the Reaction Zone Delta T of the reaction zone producing the effluent. Thus, the cooling counters the Reaction Zone Delta T of the preceding reaction zone.

A portion of the aliphatic feed is fed to each of the reaction zones in the series. Advantageously, this feed can be cooler than the preceding reaction zone effluent and serves to provide direct heat exchange. Alternatively or in addition, indirect heat exchange can be used to reduce the temperature of the effluent. The cooling medium for the indirect heat exchange may be water or any conveniently available, cooler process fluid.

The trim reaction zone typically assures that at least about 99, preferably at least about 99.5, mole percent of the olefin is reacted. In one preferred embodiment, substantially all of the olefin contained in the zone effluent that is passed to the trim reaction zone is consumed.

The effluent from the last reaction zone (or trim reaction zone if used) is directly passed to the refining system. The alkylbenzene refining system serves to remove aromatic compound, olefins, heavies, and, if present, paraffins, from the alkylated product.

In common commercial configurations for alkylbenzene, the refining assembly comprises a distillation assembly that recovers essentially all the benzene from the alkylation effluent and provides a relatively pure benzene stream as the overhead. The bottoms stream from this distillation assembly would then be passed to a distillation assembly to separate as the overhead, paraffins and unreacted olefins, and the bottoms from this second distillation assembly would be fed to a heavies distillation assembly where the alkylbenzene product is contained in the overhead. If desired, a finishing column may be used to further purify the alkylbenzene, especially after a clay treatment to remove color formers. In this type of distillation train, the bottoms stream from the crude distillation is normally fed to the distillation assembly for separating benzene.

In further detail for purposes of illustration using a dehydrogenation product stream containing both paraffins and olefins as the source of olefins for the alkylation, the benzene distillation is generally conducted with a bottoms temperature of less than about 300° C., preferably less than about 275° C., usually between about 230° C. and 270° C., and at a pressure at which the overhead is provided of between about 5 and 300, preferably between about 35 and 70, kPa gauge. The overhead generally contains less than about 2, preferably less than about 1.5, weight percent paraffins. The benzene distillation assembly may comprise one or more distillation columns. More than one overhead may be obtained from the benzene distillation assembly. For instance, a highly pure stream may be obtained for process needs such as regenerating catalysts or sorbents, e.g., having a paraffin concentration less than about 1, preferably less than about 0.1, weight percent. A lesser purity overhead may be obtained from the benzene distillation assembly, e.g., as a side draw, for use as a recycle to the alkylation reaction.

Each column used for benzene distillation may contain any convenient packing or distillation trays, but most often trays such as sieve and bubble trays, are used. Often the assembly provides at least about 5, say 6 to 70, and preferably 20 to 50, theoretical plates. The reflux ratio is often in the range of about 2:1 to 1:10, preferably about 1.5:1 to 1:5. The bottoms stream from the benzene distillation generally contains less than about 1000 ppmw, preferably less than about 50 ppmw, and sometimes less than about 5 ppmw, benzene. The benzene distillation may occur in a single column or two or more distinct columns may be used. For instance, a stripping column may be used to remove a portion, e.g., 20 to 50 percent, of the benzene and then the bottoms from the stripping column would be subjected to rectification in a subsequent column to obtain the desired separation.

The paraffin distillation is generally conducted with a bottoms temperature of less than about 300° C., preferably less than about 275° C., usually between about 250° C. and 275° C., and at a pressure at which overhead is provided of between about 5 and 110, preferably between about 10 and 50, kPa absolute. The column may contain any convenient packing or distillation trays, but most often sieve trays are used. Often the paraffins distillation assembly provides at least about 5, say 7 to 20, theoretical plates. The reflux ratio is often in the range of about 3:1 to 1:10, preferably about 1:1 to 1:3. The bottoms stream from the paraffins distillation generally contains less than about 5000, preferably less than about 500, parts by million by weight (ppmw) paraffins and preferably less than about 10, often less than about 1, ppmw benzene. The paraffins distillation may occur in a single column or two or more distinct columns may be used.

The heavy alkylate distillation is generally conducted with a bottoms temperature of less than about 300° C., preferably less than about 275° C., usually between about 250° C. and 275° C., and at a pressure of between about 0.5 and 30, preferably between about 1 and 5, kPa absolute. The column may contain any convenient packing or distillation trays, but most often structured packing is used. Often the heavy alkylate distillation assembly provides at least about 5, say 10 to 30, and preferably 10 to 20, theoretical plates. The reflux ratio is often in the range of about 2:1 to 1:5, preferably about 0.2:1 to 1:1. The overhead from the heavy alkylate distillation generally contains less than about 1000, preferably less than about 100 ppmw, and sometimes less than about 50 ppmw, total heavies.

The refining system may contain additional distillation zones, e.g., to recover additional alkylbenzene from heavies.

A crude distillation may be used to separate the effluent of one or more of the reaction zones. The crude distillation may be effected in a stand-alone vessel or may be effected in a portion of the benzene column for refining the alkylation product. Where three or more alkylation reactors are used and more than one inter-reactor crude distillation is desired, the crude distillations may be conducted in the same or different vessels. For instance, the effluents from an upstream reactor and an immediate subsequent reactor may be passed to the same crude distillation zone with a portion of the overhead being passed to the immediate subsequent reactor and the remaining portion of the overhead being passed to a third reactor that is downstream of the immediately subsequent reactor.

The invention will be further illustrated by reference to the drawings, which are not in limitation of the scope of the invention.

The drawings and description thereto are for purposes of illustration of the invention and are not in limitation thereof.

With reference to FIG. 1, a reaction assembly 100 is schematically depicted having reactor vessel 102 containing catalyst bed 104 which defines the first reaction zone in the series and receives fresh benzene feed; catalyst beds 106a, 106b, 106c and 106d defining four subsequent and in series reaction zones and catalyst bed 108 defining a trim reaction zone.

Fresh benzene is supplied via line 110. The aliphatic feedstock is provided via line 112. The temperature of the feedstock is adjusted to a desired value in heat exchanger 114, and the temperature controlled feedstock is passed via line 116 to distributor 118. The temperature of the aliphatic feedstock is selected to provide the desired cooling between reaction zones by direct heat exchange.

Distributor 118 serves to split the feedstock into controlled portions. One portion is passed via line 120 through heat exchanger 122 for combination with benzene being supplied by line 110. Heat exchanger 122 serves to heat, if necessary, the feedstock such that the combined benzene and feedstock stream being passed to catalyst bed 104 is at a suitable temperature to initiate the alkylation reaction. As the catalyst ages, it may be necessary to increase the temperature of the combined stream to catalyst bed 104. The benzene supplied via line 110 is mixed in line 126 with the aliphatic feedstock exiting heat exchanger 122 via line 124, and the mixture is passed to reactor vessel 102. Alternatively, each of the benzene and aliphatic feedstock can be separately introduced into reactor vessel 102.

Line 128a supplies a determined portion of the temperature controlled aliphatic feedstock from distributor 118 to the region 132a between catalyst beds 104 and 106a. Any suitable device, such as nozzles, venturis, spargers, and the like, may be used to facilitate distribution of the cooler aliphatic feedstock into the effluent from catalyst bed 104. Similarly, lines 128b, 128c and 128d supply portions of the aliphatic feedstock to the regions between catalyst beds 106a and 106b, 106b and 106c, and 106c and 106d, respectively. These regions are 132b, 132c, 132d, and 132e, respectively. The effluent from catalyst bed 106d is passed to trim catalyst bed 108 and the effluent from trim catalyst bed 108 is exhausted from reactor vessel 102 via line 130.

Figure 2:
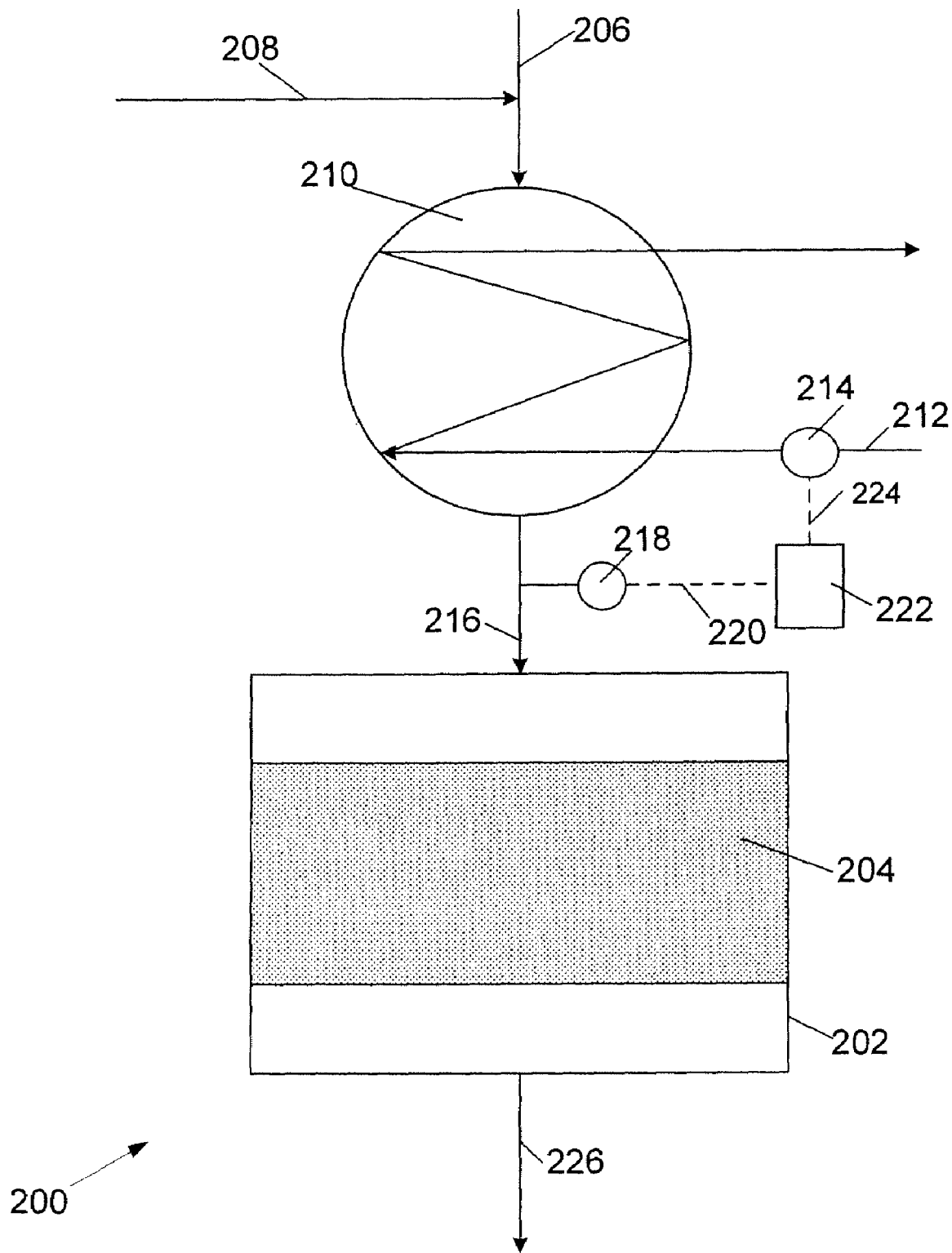
FIG. 2 is a schematic representation of a single reaction zone assembly that can be used in the apparatus and processes of this invention.

FIG. 2 is a schematic illustration of one reaction zone assembly 200 of a series of reaction zones where indirect heat exchange is used. Reaction zone vessel 202 contains catalyst bed 204 defining a reaction zone. A feedstream containing the effluent from a preceding reaction zone is provided via line 206. Aliphatic feedstock provided by a distributor is supplied via line 208 and is combined with the effluent in line 206. Because an indirect heat exchanger is used in this embodiment, the temperature of the aliphatic feedstock need not be controlled.

The combined stream in line 206 is passed to heat exchanger 210 using a cooling water stream supplied via line 212, the rate of which is controlled by valve 214. Heat exchanger 210 may be of any suitable indirect heat exchanger design including, but not limited to tube-in-shell and plate heat exchangers. In heat exchanger 210, the combined stream is cooled and exits via line 216. Temperature probe 218 responds to the temperature of the combined gases and communicates such via signal 220 to control computer 222 which in turn signals valve 214 via signal 224 to a sought position such that the rate of cooling water supply is appropriate for achieving the sought temperature of the combined stream in line 216. Line 216 directs the combined fluid to reaction zone vessel 202, and an alkylated product steam exits via line 226.

The assembly of FIG. 2 is particularly attractive for facilitating regeneration of the catalyst in a reaction zone. For instance, in an assembly containing, say, 5 reaction zones, an additional reaction zone may be provided. One reaction zone can be taken off line for regeneration and replaced with the additional reaction zone. The off-line reaction zone is subjected to regeneration conditions and it then replaces the next reaction zone to be taken off-line for regeneration.

The invention claimed is:

1. A continuous process for monoalkylating an aromatic compound of 6 to 8 carbon atoms per molecule with an aliphatic feedstock comprising paraffin and mono-olefin of 8 to 18 carbon atoms per molecule in an alkylation reactor assembly having at least three reaction zones in series, each reaction zone comprising solid alkylation catalyst and being maintained under liquid phase alkylation conditions sufficient to consume at least about 90 mass percent of the olefin to produce a zone effluent comprising arylalkane, wherein the molar ratio of total aromatic compound to total mono-olefin passed to the alkylation reactor assembly is less than about 20:1, comprising:
    a. co-currently passing said aromatic compound and a portion of the aliphatic feedstock comprising linear olefins at a first blend temperature to a preceding reaction zone to produce a preceding zone effluent, the mass ratio of said aromatic compound to said aliphatic feedstock passed to said preceding reaction zone being sufficient that the Reaction Zone Delta T of said preceding reaction zone is less than 15° C., wherein the aliphatic feedstock has a molar ratio of olefin to paraffin of between about 1:12 to 1:7;
    b. cooling the preceding zone effluent;
    c. co-currently passing at least a portion of said cooled preceding zone effluent and another portion of the aliphatic feedstock at a subsequent blend temperature to a subsequent reaction zone to produce a subsequent zone effluent comprising linear arylalkane, the mass ratio of said aromatic compound to said aliphatic feedstock passed to said subsequent reaction zone being sufficient that the Reaction Zone Delta T of said subsequent reaction zone is less than 15° C.;
    d. repeating steps (b) and (c) using the preceding zone effluent after cooling and another portion of the linear aliphatic feedstock at a blend temperature for that subsequent reaction zone a sufficient number of times to use at least 90% of the linear olefins in the aliphatic feedstock, wherein the cooling between reaction zones is at least partially effected by direct heat exchange with the portion of the aliphatic feedstock being passed to the subsequent reaction zone, said portion of the aliphatic feedstock begin provided at a cooler temperature than the preceding zone effluent, and wherein the zone effluent from the last zone is passed to a trim reaction zone without the addition of any portion of the aliphatic feedstock, comprising solid alkylation catalyst and being maintained under liquid phase alkylation conditions sufficient to consume substantially all olefin contained in the last zone effluent.

2. The process of claim 1 wherein in each of steps (a), (c) and (d), the Reaction Zone Delta T is less than 10° C.

3. The process of claim 1 wherein the molar ratio of total aromatic compound to total mono-olefin is less than about 15:1.

4. The process of claim 1 wherein the molar ratio of total aromatic compound to total mono-olefin is between about 6:1 and 12:1.

5. The process of claim 1 wherein the portion of aliphatic feedstock fed to each reaction zone is such that the difference in the Reaction Zone Delta T among the reaction zones is less than about 5° C.

6. The process of claim 5 wherein the portion of aliphatic feedstock fed to the first reaction zone is less than that portion of the aliphatic feedstock fed to at least one subsequent reaction zone of steps (b) and (c).

7. The process of claim 1 wherein the effluent from each reaction zone is cooled to reduce the temperature of the effluent by at least an amount of 60 percent of the Reaction Zone Delta T of the reaction zone producing the effluent.

\* \* \* \* \*